United States Patent [19]

Pedersen et al.

[11] Patent Number: 5,776,741
[45] Date of Patent: Jul. 7, 1998

[54] METHOD OF ENZYME IMMOBILIZATION ON A PARTICULATE SILICA CARRIER FOR SYNTHESIS INORGANIC MEDIA

[75] Inventors: Sven Pedersen, Gentofte; Anne Mørkeberg Larsen, Charlottenlund; Per Aasmul, Holte, all of Denmark

[73] Assignee: Novo Nordisk A/S, Bagsvaerd, Denmark

[21] Appl. No.: 676,367
[22] PCT Filed: Feb. 21, 1995
[86] PCT No.: PCT/DK95/00076
§ 371 Date: Jul. 19, 1996
§ 102(e) Date: Jul. 19, 1996
[87] PCT Pub. No.: WO95/22606
PCT Pub. Date: Aug. 24, 1995

[30] Foreign Application Priority Data

Feb. 21, 1994 [DK] Denmark ................. 0207/94

[51] Int. Cl.⁶ ................. C12P 7/64; C12P 7/62; C12N 11/14; C12N 9/98
[52] U.S. Cl. ................. 435/134; 435/135; 435/176; 435/187
[58] Field of Search ................. 435/174, 176, 435/180, 134, 135, 187

[56] References Cited

U.S. PATENT DOCUMENTS 4,275,081  6/1981  Coleman et al. ................. 426/33
5,342,768  8/1994  Pedersen et al. ................. 435/134

FOREIGN PATENT DOCUMENTS 0 093 027    3/1983   European Pat. Off. .
0 159 578    3/1985   European Pat. Off. .
0 140 542    4/1989   European Pat. Off. .
0 579 928 A1 5/1993   European Pat. Off. .
WO 88/02775  4/1988   WIPO .
WO 90/05778  5/1990   WIPO .
WO 94/26883  11/1994  WIPO .

OTHER PUBLICATIONS

Chemical Abstracts, 118: 55095v, 1993.
M. Norin et al., "Lipase Immobolized By Absorption", Applied Microbiology, Springer–Verlag 1988, pp. 527–530.
Fredrik Björkling et al., "A Highly Selective Enzyme–catalysed Esterification of Simple Glucosides", J. Chem. Soc., Chem. Commun., 1989, pp. 934–935.

Primary Examiner—David M. Naff
Attorney, Agent, or Firm—Steve T. Zelson, Esq.; Cheryl T. Agris, Esq.

[57] ABSTRACT

An immobilized enzyme is prepared for synthesis in a mainly organic medium devoid of free water. In one embodiment, an enzyme and liquid binder are introduced by atomization onto a particulate silica carrier having a particle size below 100 μm in a granulator and simultaneously granulating to form the immobilized enzyme. In another embodiment, a liquid enzyme composition is contacted with the particulate silica carrier to obtain a particulate immobilized enzyme having a particle size below 100 μm, the immobilized enzyme is introduced into granulator, a liquid binder is introduced into the granulator and granulation is carried out. The enzyme is preferably a lipase such as a thermostable lipase, and the immobilized lipase is used for interesterification of fats or synthesis of fatty acid esters.

24 Claims, 1 Drawing Sheet

METHOD OF ENZYME IMMOBILIZATION ON A PARTICULATE SILICA CARRIER FOR SYNTHESIS INORGANIC MEDIA

CROSS-REFERENCE TO RELATED APPLICATIONS

This application is a 35 U.S.C. 371 national application of PCT/DK95/00076 filed 21 Feb., 1995, which is incorporated herein by reference.

BACKGROUND OF THE INVENTION

The invention comprises a method for production of an immobilized enzyme preparation, comprising an enzyme applicable for organic synthesis in a mainly organic medium devoid of free water, and a use of the immobilized enzyme preparation. The most common enzyme which is applicable for organic synthesis in a mainly organic medium devoid of free water is lipase. Examples of other enzymes of this kind are proteases, amidases, esterases, oxidoreductases, and nitrilases. In the following the invention usually will be described with reference to lipase as the predominant example of an enzyme which is applicable for organic synthesis in a mainly organic medium devoid of free water. The term "organic synthesis" is to be understood as generally accepted in organic chemistry. Thus, typical examples of organic syntheses included in the scope of the invention are the following: reesterifications, transesterifications, interesterifications, acylations, epoxidations, aminolyses, ammoniolyses, oxidations, and reductions. The term "mainly organic medium devoid of free water" is to be understood as a one phase medium, the organic part of which amounts to at least 50% w/w.

Immobilized lipase preparations are used as catalysts for interesterification and other fat related processes, e.g. cocoa butter substitute production. In case of a batch reaction the catalyst has to be separated from the reaction mixture for reuse when the reaction is finished. Thus, a good filtrability of the catalyst is needed for satisfactory performance.

WO 90/05778 describes a method for production of an immobilized lipase preparation useable for e.g. margarine production. This preparation comprises a macroporous silica carrier.

EP 140 542 describes an immobilized lipase preparation for interesterification of fats. This preparation comprises an anion exchange resin carrier.

Both these prior art immobilized lipase preparations suffer from the disadvantage that they are expensive. Especially in relation to the production of margarine, which is produced in millions of tons per year on a global basis, it is important to minimize production costs.

Thus, the purpose of the invention is the provision of a method for production of a cheap immobilized enzyme preparation which should exhibit technical properties equal to or almost equal to the prior art immobilized enzyme preparations, especially in regard to filtrability after a finished batchwise margarine production and in regard to a low pressure drop in columns for continuous performance, in case the enzyme is a lipase, and of a use of such immobilized enzyme preparation.

SUMMARY OF THE INVENTION

The method according to the invention for production of an immobilized enzyme preparation comprising an enzyme applicable for organic synthesis in a mainly organic medium devoid of free water, is characterized by the fact that a liquid enzyme composition and a particulate silica carrier with a particle size below around 100 µm is used as materials to be introduced into a granulator or extruder, whereafter a granulation or an extrusion is carried out. The liquid enzyme composition can be non-aqueous, e.g. on alcoholic basis, or aqueous. The particulate silica carrier can exhibit a broad particle size distribution, e.g. between around 5 µm and 100 µm. In this specification with claims "silica" is to be understood as either silica or a silicate, e.g. magnesium silicate. It is to be understood that the invention both comprises the situation, where a particulate immobilized lipase composition with a particle size distribution similar to the particle size distribution of the particulate silica carrier is first produced, whereafter the granulation or extrusion is carried out (vide Examples 6 and 7), and the situation, where the production is carried out in one step only (vide Examples 1 to 5). Also, it is to be understood that the enzyme may act as a binder during the granulation or extrusion, and/or that a specific binding agent can be added, e.g. gelatin or polyvinylpyrrolidone. During the method according to the invention preferably an atomization has to be carried out, usually an atomization of the liquid enzyme composition and/or an atomization of the binding agent in liquid form. Also, it is to be understood that the apparatus used in the method according to the invention is of no special importance to the invention, inasmuch as any granulator, e.g. a fluid bed spray granulator, or any extruder can be used.

A powdered immobilized lipase preparation on silica basis is described, e.g. in WO 88/02775, page 11, lines 21–24. This immobilized lipase preparation is completely unfit for both batchwise and continuous fat related processes, due to poor filtrability after a batch process and generation of a high pressure loss during a continuous column process.

Immobilized lipase preparations are described in EP 579928 and in Appl. Microbiol. Biotechnol. (1988) 28:527–530, but none of these prior art lipase preparations comprise a silica carrier.

In Chem. Abstract Vol. 118 (1993): 55095v an immobilized lipase preparation on a silica carrier is described. However, the method according to the invention comprising particle size of the carrier and granulation or extrusion is not described.

Surprisingly it has been found that the immobilized enzyme preparation prepared in accordance with the method according to the invention in the first place is dramatically cheaper than the comparable prior art immobilized enzyme preparations, and in the second place that it exhibits technical properties equal to or almost equal to the prior art immobilized enzyme preparations, e.g. in regard to filtrability after a batchwise fat related process and generation of a low pressure loss during a continuous fat related process, if the enzyme is a lipase.

Figure 1:
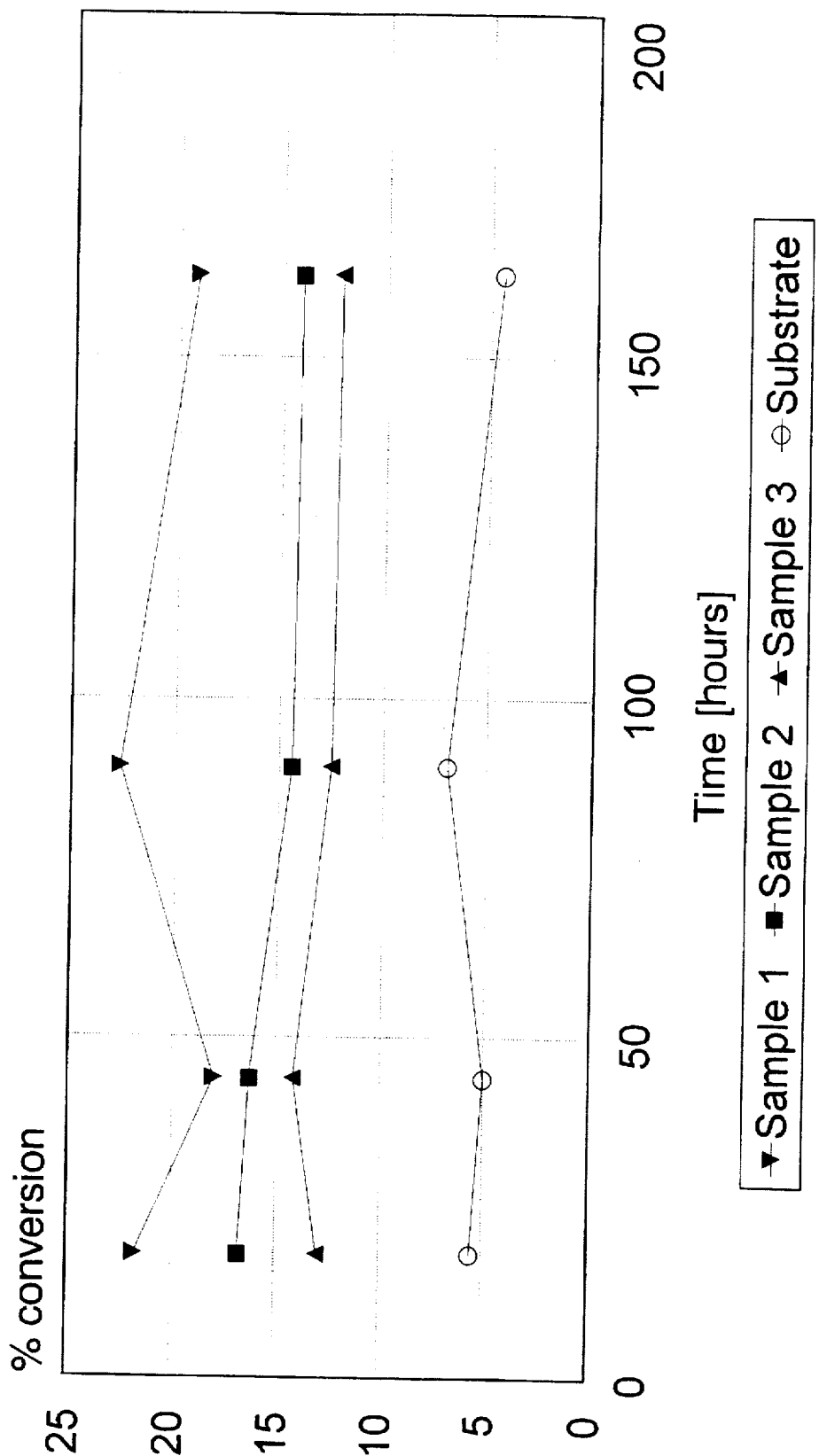
FIG. 1, which is directly related to Example 9, shows percent conversion depending on time in relation to an ester synthesis performed as a continuous column operation.

DESCRIPTION OF THE PREFERRED EMBODIMENTS;

A preferred embodiment of the method according to the invention is characterized by the fact that the enzyme is a lipase.

A preferred embodiment of the method according to the invention is characterized by the fact that the lipase in the liquid lipase composition is a thermostable lipase.

A preferred embodiment of the method according to the invention is characterized by the fact that the lipase in the liquid lipase composition is produced by cultivation of a microorganism containing a gene encoding for and expressing a lipase derived from a strain of Humicola species, *Candida antarctica* or *Rhizomucor miehei*.

A preferred embodiment of the method according to the invention is characterized by the fact that the proportion between the amount of the liquid lipase composition and the weight of particulate silica carrier is at least 100.000 LU/g of carrier (dry weight). LU is the lipase activity unit defined in AF 95.½-GB, which can be obtained on request from Novo Nordisk A/S. The LU assay uses tributyrin as a substrate for determination of the lipase activity.

A preferred embodiment of the method according to the invention is characterized by the fact that the silica has a purity of at least 50%, preferably at least 75%.

A preferred embodiment of the method according to the invention is characterized by the fact that a granulator is used, preferably a high speed mixer or a mixer granulator.

A preferred embodiment of the method according to the invention is characterized by the fact that a liquid composition of a binder, preferably gelatin or polyvinylpyrrolidone, is introduced by atomization into the granulator or extruder during the granulation or extrusion.

A preferred embodiment of the method according to the invention is characterized by the fact that the granulation or extrusion is carried out for production of the immobilized lipase preparation with a particle size distribution corresponding to an amount of at least 90% between 50 µm and 2.000 µm.

The use of the immobilized enzyme preparation prepared by means of the method according to the invention is for the process catalyzed by the enzyme.

The use of the immobilized lipase preparation prepared by means of the method according to the invention is for fat related processes. It is to be understood that such fat related processes can be performed batchwise or continuously. When performed batchwise it has been found that the immobilized lipase preparation produced by means of the method according to the invention exhibits a satisfactory filtrability when the enzymatic process has come to an end, and when performed continuously it has been found that the immobilized lipase preparation produced by means of the method according to the invention exhibits a good physical strength resulting in a satisfactory performance of the column.

A preferred embodiment of the use according to the invention is for interesterification of fats and is characterized by the fact that liquid fats or fatty mixtures, including free fatty acids or fatty acid esters, are contacted with the immobilized lipase preparation.

A preferred embodiment of the use according to the invention is for synthesis of glycerides or other fatty acid esters and is characterized by the fact that mixture of glycerol or substituted glycerols or other types of alcohols and free fatty acids is contacted with the immobilized lipase preparation.

A preferred embodiment of the use according to the invention is for synthesis of glycolipids. The synthesis of glycolipids with immobilized lipase reparations in general is described in Björkling, F. et al. (1989), J. Chem. Soc., Chem. Commun., p. 934–935.

The invention will be illustrated by the following examples.

All manufacturing examples (1–8) illustrate the batchwise embodiment of the method according to the invention. For production in industrial scale ordinarily the continuous embodiment will be preferred. Example 9 is a use example.

The use according to the invention is illustrated indirectly in Examples 1–8, in consideration of the fact that every BAUN determination illustrates the use (interesterification) according to the invention. The use according to the invention is illustrated directly in Example 9.

EXAMPLES

EXAMPLE 1

65 g of a powder of synthetic magnesium silicate, Celkate T-21 (Manville) was introduced into a high speed mixer with an impeller which can be operated with a speed of 900 rpm. 75 g of *Humicola lanuginosa* lipase liquid concentrate (prepared according to Danish Patent No. 157560, with *Humicola lanuginosa* DSM 3819, dry substance content 30%, with an activity of 700.000 LU/ml) was continuously atomized onto the silica powder over a period of approx. five minutes with running impeller. The formed granulate was dried overnight at room temperature and sieved (300–700 µm). The moisture content was adjusted to 10% and the sample analyzed to 2.6 BAUN/g. The lipase activity assay expressed in BAUN (Batch Acidolysis Units Novo) measures the initial rate of incorporation of decanoic acid into high oleate sunflower oil (10% water, 70° C.). A detailed description of the method (MP 9410704) is available on request from Novo Nordisk A/S. The assay was performed without magnetic stirring, but in a shaking water bath.

EXAMPLE 2

65 g of Celkate T-21 was introduced into a high speed mixer as indicated in Example 1. 25 g of *Humicola lanuginosa* lipase liquid concentrate as indicated in Example 1 was continuously atomized onto the powder with running impeller. Hereafter, 50 g of the *Humicola lanuginosa* lipase liquid concentrate with 3% (w/w) Kollidon K25 polyvinylpyrrolidone (BASF) was atomized onto the powder. The formed granulate was dried overnight at room temperature and sieved (300–700 µm). The moisture content was adjusted to 10% and the sample analyzed to 0.5 BAUN/g.

EXAMPLE 3

40 g of a powder of a calcinated diatomaceous earth, Clarcel CBL 3 (Ceca S.A.) was introduced into a high speed mixer as indicated in Example 1. 11 g of *Humicola lanuginosa* lipase liquid concentrate as indicated in Example 1 was continuously atomized onto the powder with running impeller. Hereafter, 47 g of the *Humicola lanuginosa* lipase with 3% (w/w) Kollidon K25 was atomized onto the powder with running impeller. The formed granulate was dried overnight at room temperature and sieved (300–700 µm). The moisture content was adjusted to 10% and the sample analyzed to 2.4 BAUN/g.

EXAMPLE 4

50 g of Clarcel CBL 3 was introduced into a high speed mixer as indicated in Example 1. 72 g of *Humicola lanuginosa* lipase liquid concentrate as indicated in Example 1 with 5% (w/w) gelatin (ASF gelatin, Sanofi Bio-Industries) was continuously atomized onto the powder liquid concentrate as indicated in Example 1. The formed granulate was dried overnight at room temperature and sieved (300–700 µm). The moisture content was adjusted to 10% and the sample analyzed to 5.1 BAUN/g.

EXAMPLE 5

30 g of Clarcel CBL 3 and 20 g of talc powder was introduced into a high speed mixer as indicated in Example 1. 20 g of *Humicola lanuginosa* lipase liquid concentrate as indicated in Example 1 was continuously atomized onto the powder liquid concentrate as indicated in Example 1. Hereafter, 28 g of the *Humicola lanuginosa* lipase concentrate with 2% (w/w) Methocel A-15 methylcellulose (Dow) was atomized onto the powder with running impeller. The formed granulate was dried overnight at room temperature and sieved (300–700 μm). The moisture content was adjusted to 10% and the sample analyzed to 7.7 BAUN/g.

EXAMPLE 6

250 g of Celkate T-21 was washed with 3 volumes of 0.1M acetate buffer, pH 4.5, for 30 minutes, followed by vacuum filtration. *Humicola lanuginosa* lipase concentrate as indicated in Example 1 in an amount corresponding to 500.000 LU/g of Celkate T-21 was added together with 3 volumes of 0.1M acetate buffer, pH 4.5, and stirred for two hours at room temperature. After vacuum filtration the immobilized lipase was dried for 24 hours at room temperature, the moisture content adjusted to 10% and analyzed to 14.3 BAUN/g. The filtrate contained 27565 kLU, corresponding to an adsorption of 78% (or 390 kLU/g).

65 g of the thus dried immobilized lipase on Celkate T-21 powder was introduced into a high speed mixer as indicated in Example 1. 55 g of a 5% (w/w) gelatin solution was atomized onto the powder with running impeller. Hereafter, 0.1 g of Aerosil 200 silicium dioxide (Degussa) was added. The formed granulate was dried at room temperature and sieved (300–700 μm). The moisture content was adjusted to 10% and analyzed to 5.9 BAUN/g.

EXAMPLE 7

200 g of Clarcel CBL 3 was washed with 3 volumes of 0.1M acetate buffer, pH 4.5, for 30 minutes, followed by vacuum filtration. *Humicola lanuginosa* lipase concentrate as indicated in Example 1 in an amount corresponding to 500.000 LU/g of Clarcel CBL 3 was added together with 3 volumes of 0.1M acetate buffer, pH 4.5, and stirred for two hours at room temperature. After vacuum filtration the immobilized lipase was washed two times with 2–3 volumes of 0.1M acetate buffer, pH 4.5, and two times with deionized water. The filtrates contained 82761 kLU in total corresponding to an adsorption of 17% (or 86 kLU/g). The immobilized lipase was dried for 24 hours at room temperature and analyzed to 13.4 BAUN/g.

55 g of the thus washed immobilized lipase on Clarcel CBL 3 powder was introduced into a high speed mixer as indicated in Example 1.61 g of a solution containing 2% (w/w) gelatin and 1% (w/w) Methocel A-15 methylcellulose (Dow) was continuously atomized onto the powder with running impeller. Hereafter, 0.1 g of Aerosil 200 silicium dioxide (Degussa) was added. The formed granulate was dried at room temperature and sieved (300–700 μm). The moisture content was adjusted to 10% and analyzed to 8.4 BAUN/g.

Another portion, i.e. 59 g of the thus washed immobilized lipase on Clarcel CBL 3 powder was introduced into a high speed mixer as indicated in Example 1.59 g of a 5% (w/w) gelatin solution was continuously atomized onto the powder with running impeller. Hereafter, 0.1 g of Aerosil 200 silicium dioxide (Degussa) was added. The formed granulate was dried at room temperature and sieved (300–700 μm). The moisture content was adjusted to 10% and analyzed to 10.1 BAUN/g.

EXAMPLE 8

This is a manufacturing example as Examples 1–7, but with another lipase producing microorganism.

Preparation of Sample 1: 12.9 g of *Candida antarctica* B lipase freeze dried powder with an activity of 250.000 LU/g and 1.4 g of Kollidon K25 was dissolved in 51 ml of deionized water. 50 g of Celkate T-21 was introduced into a high speed mixer as indicated in Example 1 and the above indicated solution of *Candida antarctica* B lipase was continuously atomized onto the powder with running impeller. The formed granulate was dried overnight at room temperature and sieved (300–1000 μm).

Preparation of Sample 2: 12.9 g of *Candida antarctica* B lipase and 0.86 g of Methocel A-15 was dissolved in 51 ml of deionized water. 50 g of Celkate T-21 was introduced into a high speed mixer and the above solution was continuously atomized onto the powder with running impeller. The formed granulate was dried overnight at room temperature and sieved (300–1000 μm).

Preparation of Sample 3: 12.8 g of *Candida antarctica* B lipase and 0.81 g of Kollidon K25 was dissolved in 48 ml deionized water. 50 g of Celkate T-21 was introduced into a high speed mixer and the above solution was continuously atomized onto the powder with running impeller. The formed granulate was dried overnight at room temperature and sieved (300–1000 μm).

EXAMPLE 9

This is a use example with the preparation according to Example 8, associated with FIG. 1.

The three samples described in Example 8 were evaluated in columns by continuous synthesis of ethyl glucosid esters (EGE) by reacting ethyl glucosid (EG) with decanoic acid.

| Reaction conditions: | | |
|---|---|---|
| Column dimensions: | diameter = 1.5 cm; length = 20 cm | |
| Sample size: | 5.0 g | |
| Substrate: | Ethyl glucosid*) | 4.98 kg |
|  | Decanoic acid | 4.92 kg |
|  | Tertiary butanol 25% | 3.30 kg |
| Temperature: | 60° C. | |
| Flow: | 30 g/h | |
| Time: | 162 hours | |

*)Synthesized by reacting ethanol and D-glucose in the presence of a cation exchanger Samples were taken after 18, 44, 90, and 162 hours and the content of EGE and EG was measured on HPLC and % conversion calculated. The results are shown in FIG. 1. Moreover, it was noticed that the physical stability of the samples was good.

We claim:

1. A method for producing an immobilized enzyme preparation applicable for organic synthesis in a mainly organic medium devoid of free water, comprising:

introducing an enzyme and a binder in liquid form by atomization onto a particulate silica carrier having a particle size below 100 μm in a granulator, and simultaneously carrying out a granulation to form the immobilized enzyme preparation.

2. The method according to claim 1, wherein the enzyme is a lipase.

3. The method according to claim 2, wherein the lipase is a thermostable lipase.

4. The method according to claim 2, wherein the lipase is derived from a strain of Humicola species, *Candida antarctica* or *Rhizomucor miehei*.

5. The method according to claim 2, wherein the ratio between the lipase and the particulate silica carrier corresponds to an activity of at least 100.000 LU/g of carrier (dry weight).

6. The method according to claim 1, wherein the silica has a purity of at least 50%.

7. The method according to claim 6, wherein the silica has a purity of at least 75%.

8. The method according to claim 1, wherein the granulator is a high speed mixer or a mixer granulator.

9. The method of claim 1, wherein the binder is gelatin or polyvinyl pyrrolidone.

10. A method for producing an immobilized enzyme preparation applicable for organic synthesis in a mainly organic medium devoid of free water, comprising:

contacting a liquid enzyme composition with a particulate silica carrier having a particle size below 100 μm to obtain a particulate immobilized enzyme preparation having a particle size below 100 μm, and introducing the particulate immobilized enzyme preparation into a granulator, introducing a liquid comprising a binder by atomization into the granulator, and carrying out a granulation.

11. The method according to claim 10, wherein the enzyme is a lipase.

12. The method according to claim 11, wherein the lipase is a thermostable lipase.

13. The method according to claim 11, wherein the lipase is derived from a strain of Humicola species, *Candida antarctica* or *Rhizomucor miehei*.

14. The method according to claim 11, wherein the ratio between the lipase and the particulate silica carrier corresponds to an activity of at least 100,000 LU/g of carrier (dry weight).

15. The method according to claim 10, wherein the silica has a purity of at least 50%.

16. The method according to claim 15, wherein the silica has a purity of at least 75%.

17. The method according to claim 10, wherein the granulator is a high speed mixer or a mixer granulator.

18. The method of claim 10, wherein the binder is gelatin or polyvinyl pyrrolidone.

19. A method for interesterification of fats, comprising contacting a fatty mixture containing a free fatty acid or a fatty acid ester with an immobilized lipase preparation which is produced by:

introducing a lipase and a binder in liquid form by atomization onto a particulate silica carrier having a particle size below 100 μm in a granulator, and simultaneously carrying out a granulation to form the immobilized lipase preparation.

20. A method for interesterification of fats, comprising contacting a fatty mixture containing a free fatty acid or a fatty acid ester with an immobilized lipase preparation which is produced by:

contacting a liquid enzyme composition with a particulate silica carrier having a particle size below 100 μm to obtain a particulate immobilized lipase preparation having a particle size below 100 μm, and introducing the particulate immobilized enzyme preparation into a granulator, introducing a liquid comprising a binder by atomization into the granulator, and carrying out a granulation.

21. A method for the synthesis of a fatty acid ester comprising contacting an alcohol and a free fatty acid with an immobilized lipase preparation which is produced by:

introducing a lipase and a binder in liquid form by atomization onto a particulate silica carrier having a particle size below 100 μm in a granulator, and simultaneously carrying out a granulation to form the immobilized lipase preparation.

22. The method of claim 21, wherein the fatty acid ester is a glyceride and the alcohol is glycerol or a substituted glycerol.

23. A method for the synthesis of a fatty acid ester comprising contacting an alcohol and a free fatty acid with an immobilized lipase preparation which is produced by:

contacting a liquid enzyme composition with a particulate silica carrier having a particle size below 100 μm to obtain a particulate immobilized lipase preparation having a particle size below 100 μm, and introducing the particulate immobilized enzyme preparation into a granulator, introducing a liquid comprising a binder by atomization into the granulator, and carrying out a granulation.

24. The method of claim 23, wherein the fatty acid ester is a glyceride and the alcohol is glycerol or a substituted glycerol.

* * * * *